US 6,695,868 B2

(12) United States Patent
Looney et al.

(10) Patent No.: US 6,695,868 B2
(45) Date of Patent: Feb. 24, 2004

(54) SLED ASSEMBLY FOR USE WITH A SURGICAL RETRACTOR AND MEDICAL INSTRUMENT AND METHODS RELATED THERETO

(75) Inventors: Christopher S. Looney, Alpharetta, GA (US); Justin Wolfe, Roswell, GA (US); Kirk W. Charles, Austell, GA (US); Jeffrey T. Stout, Austell, GA (US); Saro Nalbandian, Atlanta, GA (US); Stephen J. Zwonitzer, Atlanta, GA (US); Jennie H. Brown, Providence, RI (US); Lawrence F. Travers, Westport, MA (US); Thomas E. Martin, Riverside, RI (US); Michael A. Valerio, Wrentham, MA (US)

(73) Assignee: Teleflex-CT Devices Incorporated, Plymouth Meeting, PA (US)

( * ) Notice: Subject to any disclaimer, the term of this patent is extended or adjusted under 35 U.S.C. 154(b) by 0 days.

(21) Appl. No.: 10/098,207

(22) Filed: Mar. 14, 2002

(65) Prior Publication Data
US 2002/0099272 A1 Jul. 25, 2002

Related U.S. Application Data

(63) Continuation of application No. 09/489,314, filed on Jan. 21, 2000, which is a continuation-in-part of application No. 09/345,859, filed on Jul. 1, 1999, now Pat. No. 6,348,036.
(60) Provisional application No. 60/117,333, filed on Jan. 24, 1999.

(51) Int. Cl.$^7$ ................................................. A61B 1/32
(52) U.S. Cl. ....................................................... 606/232
(58) Field of Search ................................. 600/201, 210, 600/227, 228, 231, 232, 233, 234, 235

(56) References Cited

U.S. PATENT DOCUMENTS 6,102,854 A * 8/2000 Cartier et al. ............... 600/228

* cited by examiner

Primary Examiner—Pedro Philogene
Assistant Examiner—David A Bonderer
(74) Attorney, Agent, or Firm—Dochart LLP; John W. Ryan

(57) ABSTRACT

The present invention relates to an improved sled assembly for use with surgical retractors and devices for stabilizing a predetermined area of the body during a surgical procedure, more particularly to surgical retractors and stabilizing devices used in connection with coronary artery bypass grafting surgical procedures, and more specifically to a sled assembly having a sled member and mounting mechanism thereon for use with surgical retractors and medical or stabilizing devices especially configured for use with each other for such surgical procedures wherein the retractor includes an external rail system which enables the surgeon to position a stabilization arm system on either of the arms or the rack segment of the retractor and also includes a sled assembly which releasably controls the rotation of the stabilizing device in a three dimensional directions relative to the retractor upon actuation of a single knob or actuator.

57 Claims, 11 Drawing Sheets

SLED ASSEMBLY FOR USE WITH A SURGICAL RETRACTOR AND MEDICAL INSTRUMENT AND METHODS RELATED THERETO

The present application is a continuation of U.S. Ser. No. 09/489,314 filed on Jan. 21, 2000 which is continuation-in-part of U.S. Ser. No. 09/345,859 filed on Jul. 1, 1999 now U.S. Pat. No. 6,348,036 which is a continuation-in-part of U.S. Ser. No. 60/117,333 filed on Jan. 24, 1999.

FIELD OF INVENTION

The present invention relates to surgical refractors and devices for stabilizing a predetermined area of the body during a surgical procedure, more particularly to surgical retractors and stabilizing devices used in connection with an improved sled assembly and used in coronary artery bypass grafting surgical procedures, and more specifically to surgical retractors and stabilization devices especially configured for use with each other for such surgical procedures.

BACKGROUND OF THE INVENTION

Diseases of the cardiovascular system affect millions of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system leading to the heart.

One technique for treating such a blockage or restriction is a surgical procedure known as a coronary artery bypass graft procedure, which is more commonly known as "a heart bypass" operation. The surgical correction of occluded or stenosed coronary arteries by means of bypass grafting are probably still the most common procedures performed today, especially when multiple grafts are needed.

In the coronary artery bypass graft procedure, the surgeon either removes a portion of a vein from another part of the body for grafting or detaches one end of an artery and connects that end past the obstruction in the coronary artery while leaving the other end attached to the arterial supply. When using a vein from another part of the body, the surgeon installs this portion at points that bypass the obstruction. In both cases, the objective is to restore normal blood flow to the heart.

In addition, when using this technique the surgeon makes a long incision down the middle of the chest, saws through the sternum, spreads the two halves of the sternum apart and then performs several procedures necessary to connect the surgical patient to a cardiopulmonary bypass machine to continue the circulation of oxygenated blood to the rest of the body while the heart is stopped and the graft is being sewn in place although such a procedure is one common technique for treatment, the procedure is lengthy, traumatic, considerably expensive and can damage the heart, the central nervous system and the blood supply.

Interventional techniques, such as percutaneous transluminal angioplasty (PTCA) have gained popularity as the method of choice for therapy of atherosclerosis occlusions for several reasons. The transluminal approach is a minimally invasive technique that subjects the patient to less trauma and less recovery time, especially when compared to bypass grafts which utilize homologous tissue, such as saphenous vein grafts. Also, the patient often suffers complications at the donor site of the graft that may be worse than the sternotomy and anastomosis.

Although PTCA procedures are often successful, complications such as restenosis or thrombosis and embolism can occur. Restenosed vessels may often require surgical intervention for correction. The surgical correction of restenosis like the conventional coronary bypass surgical procedure requires the heart to be stopped and the patient placed on a heart/lung bypass machine during the procedure.

In recent years, and in an effort to reduce expense, risk and trauma to the patient, physicians have turned to minimally or less invasive surgical approaches to the heart, such as intercostal and endoscopic access to the surgical site. With such procedures, the heart is beating during the surgical procedure. Thus, there is no need for any form of cardiopulmonary bypass and there is no need to perform the extensive surgical procedures necessary to connect the patient to such a bypass machine.

Such attempts at performing minimally invasive bypass grafting on a beating heart, however, have been thought of as being tedious, dangerous and difficult because of the delicate nature of the surgical procedure, the lack of adequate access through a reduced surgical field, and the lack of a way to adequately stabilize and reduce tissue movement at the graft site. Because these procedures are performed while the heart muscle is continuing to beat, the blood continues to flow and the heart continues to move in three dimensional movement while the surgeon is attempting to sew the graft in place. Also, the surgical procedure to install the graft requires placing a series of sutures through an extremely small vessel and onto tissue that continues to move during the procedure. It is necessary that these sutures be fully and securely placed so the graft is firmly in position and does not leak.

There is disclosed in U.S. Pat. No. 5,730,757, an access platform for the dissection of an internal mammary artery. The described access platform has first and second blades interconnected to a spreader member that laterally drives the blades apart or together and support pads interconnected to the first blade. A torsional member is operably interconnected to the first blade and the spreader member and is used to vertically displace the first blade in either direction. Thus, increasing the surgeon's working space and visual access for the dissection of the internal mammary artery. A tissue retractor interconnected to the blades is used to draw the soft tissue around the incision away from the surgeon's work area. It is further provided that the access platform can include a port that can be used to mount a heart stabilizer instrument.

There also is described in U.S. Pat. No. 5,875,782 granted to Ferrari et al. and U.S. Pat. No. 5,894,843 granted to Benetti et al. an apparatus for stabilizing the predetermined area on a heart or other organ of a patient to enable a surgical procedure on a beating heart. The apparatus includes a bifurcated member having two elongated prongs and an elongated handle. The handle segment can be movably attached to a rib retractor so that a person is not required to hold the handle segment. In one disclosed embodiment, the apparatus further includes a device to hold the bifurcated member in a position against the surface of the heart sufficiently so that a stabilizing force is applied against the heart and contraction of the heart does not cause either vertical or horizontal motion at the target site during the surgical procedure.

There also is described in U.S. Pat. No. 5,836,311 granted to Borst et al. an apparatus for stabilizing the predetermined area on a heart or other organ of a patient to enable a surgical procedure on a beating heart. The apparatus includes a single legged or bifurcated member having a plurality of suction members thereon which are attached to the surface of the heart using suction pressure. The arm portion of this device can be movably attached to a rib retractor or other surgical device so a person is not required to hold the handle segment and the suction device may be locked into position against the surface of the heart.

It is therefore desirable to provide a new system and devices related thereto for stabilizing a predetermined area of the body, such as the heart and methods related thereto. It is particularly desirable to provide such a system and devices thereto that are less complex and more user friendly in comparison to prior art devices. Such systems and devices thereto preferably are simple in construction and less costly than prior art devices.

SUMMARY OF THE INVENTION

The present invention features a system for retracting, stabilizing or manipulating a predetermined area of a body. The system includes a sled assembly for use with a surgical retractor, a stabilization arm system or apparatus and a tissue support or stabilization device, and methods of use related thereto. Also featured is a system that supports any of a number of surgical implements, for example a diaphragm retractor, a valve retractor, a light or suction device for use during a surgical procedure. The stabilization system and related devices and apparatuses thereto that are featured herein are particularly advantageous for use in performing off-pump coronary artery bypass grafting procedures in which the heart remains beating during the surgical procedure and/or valve surgery where the heart is stopped. One advantage of the present invention relates to the use of the external rail system on the arms of the retractor and even more preferably also on the rack segment of the retractor. The use of the external rail systems allows the stabilization arm system to be attached to the retractor at any desired location and does not require that the stabilization arm system be slid on from an end of an arm or specially attached in certain specific locations. Additionally, the sled assembly of the present invention allows for a full range of three dimensional motion of the stabilization arm which is controlled by a single knob that is easily manipulated by the surgeon.

In a general aspect, the stabilization system of the present invention is preferably used for stabilizing a predetermined area of a patient. This system preferably includes a retractor, a stabilization device for locally stabilizing the predetermined area and a stabilization arm system that functionally secures the stabilization device to the retractor. The retractor preferably includes a rail system having two arms and a rack segment. The rack segment interconnects the two arms, for selectively spacing the two arms from each other and for maintaining the two arms in a desired fixed relationship. In a preferred form of the present invention, the two arms and rack segment are configured to receive the connector of the stabilization arm system at the desired location thereon.

The stabilization device preferably includes a device of the type commonly known as the Cohn Cardiac Stabilizer marketed by the Genzyme Corporation of Cambridge, Mass., although horseshoe or suction type devices may also be used. The preferred form of the stabilization device is a generally square or rectangularly shaped member having a planar surface with centrally located opening therein. This opening is the area through which the surgeon performs the anastomosis or other procedure on the tissue of the beating heart. The stabilization device is preferably a two piece member so that once the anastomosis is completed, the pieces may be separated to remove the device from around the anastomosis. As described more fully below, flexible tapes are sutured through the tissue and then threaded through the stabilizing device. Once the stabilization device is positioned in the desired orientation and location in contact with the tissue, the flexible tapes are then pulled snug through the opening of the stabilization device to provide a system which minimizes the overall movement of the predetermined area of the tissue.

The stabilization arm system preferably includes an elongated handle having a first end and a distal connector thereon for releasably connecting the stabilization device to the elongated handle first end. This connection allows the stabilization device to be pivotally and slidably moved to a desired position into contact with the predetermined area of the tissue of the patient. The stabilization arm system also includes the sled assembly having a sled member for removably securing the stabilization arm system to at least one of the rails on the retractor arms and/or the rack segment of the retractor and which is preferably slidable along the retractor and a mounting mechanism which releasably engages the handle segment.

According to one aspect of the present invention, the arms of the retractor are configured with a front edge and a step in the top surface thereof to form an elongated rail surface along substantially the entire length thereof. The step is preferably spaced apart a predetermined and consistent distance from the front edge and is also located on the interconnecting or rack segment of the retractor. Also, the stabilization arm system preferably includes the sled assembly having a sled member which is configured to removably engage the front edge and the step at any desired location on one or more of the arms or the rack segment of the retractor. The sled member preferably includes a lever for selectively engaging the step and front edge on the arm or rack segment of the retractor so the sled member is removably and slidably secured to the arms or the rack segment.

In another aspect of the present invention, there is featured a surgical retractor including two arms, a rack segment and a plurality of sternal blades with at least one blade extending downwardly from each arm. Each blade includes an upper portion adjacent to the bottom surface of the arm and a lower section extending distally of the arm. A slot on the bottom surface of the arms includes a tapered surface adjacent to the front edge thereof to facilitate the placement of the blades on the arms. A lip surface is also located adjacent to the slots on the bottom surface of the arms to securely retain the blades on the bottom surface of the arms during the procedure while still allowing the blades to be easily removable for initial positioning and subsequent sterilization following the procedure.

In yet another aspect of the present invention there is featured a sled assembly preferably having a sled member and mounting mechanism that allows the user to retain the stabilization arm system in sliding and fixed relationships relative to the retractor and patient while also allowing for the rotation of the sled member relative to the mounting mechanism and therefore, allowing the rotation of the stabilization arm and stabilization device, with respect to the retractor by manipulating a single knob. Furthermore, the lever on a lower portion of the sled assembly allows the sled member to be slidably and fixedly positioned along the arms and rack segment of the retractor. Each of these features enables the user to determine the optimum position for the stabilization arm and stabilization device while ensuring that the surgeon's view of the operative area is not unnecessarily obstructed. Additionally, these features allow the present invention to be used in many different medical procedures because of the versatility of system set up and orientation of the components of this invention.

Other aspects and embodiments of the invention are more fully discussed below.

BRIEF DESCRIPTION OF THE DRAWINGS

For a fuller understanding of the nature and desired objects of the present invention, reference is made to the following detailed description taken in conjunction with the accompanying drawing figures wherein like reference numbers denote corresponding parts throughout the several views and wherein.

DESCRIPTION OF THE PREFERRED EMBODIMENT

Figure 1:
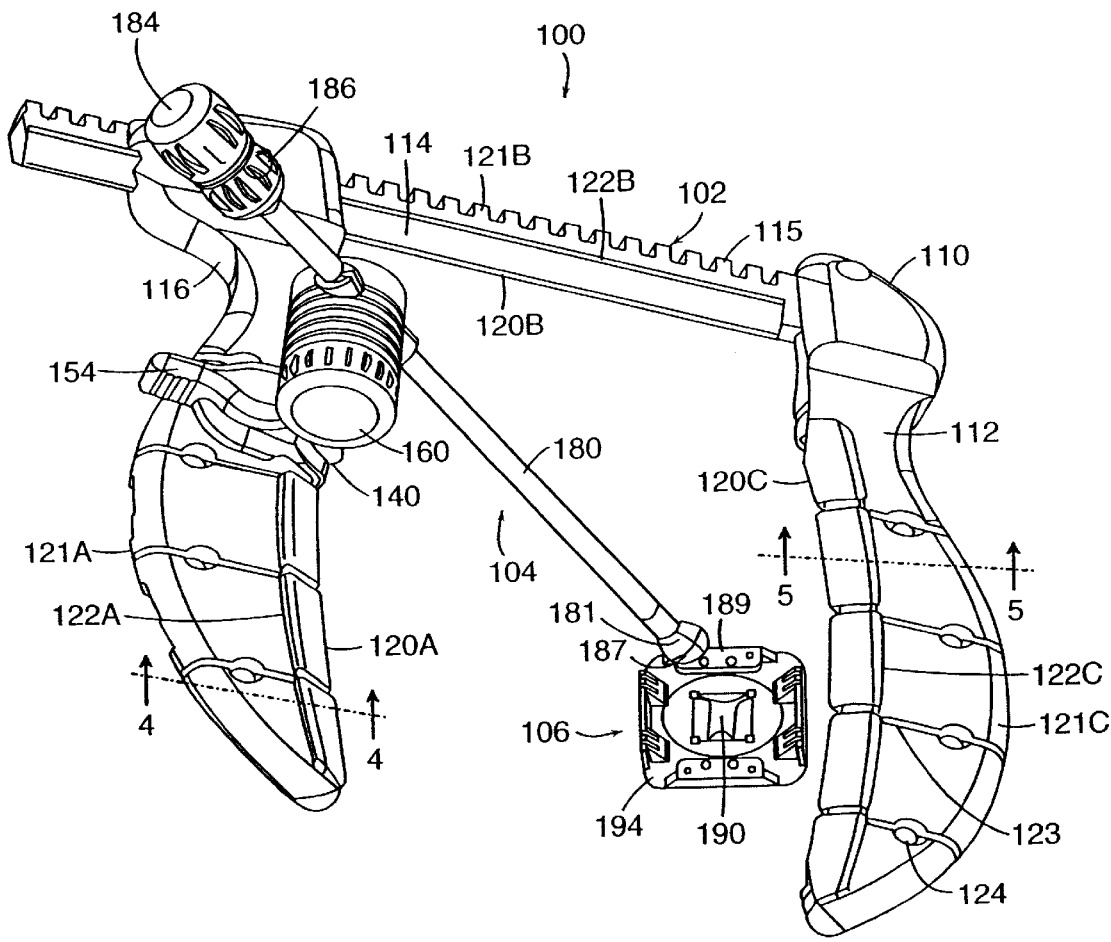
FIG. 1 is a perspective view of a stabilization system that assists in the stabilization of a predetermined area of a body according to a first aspect of the present invention with the handle removed for clarity.
Figure 2:
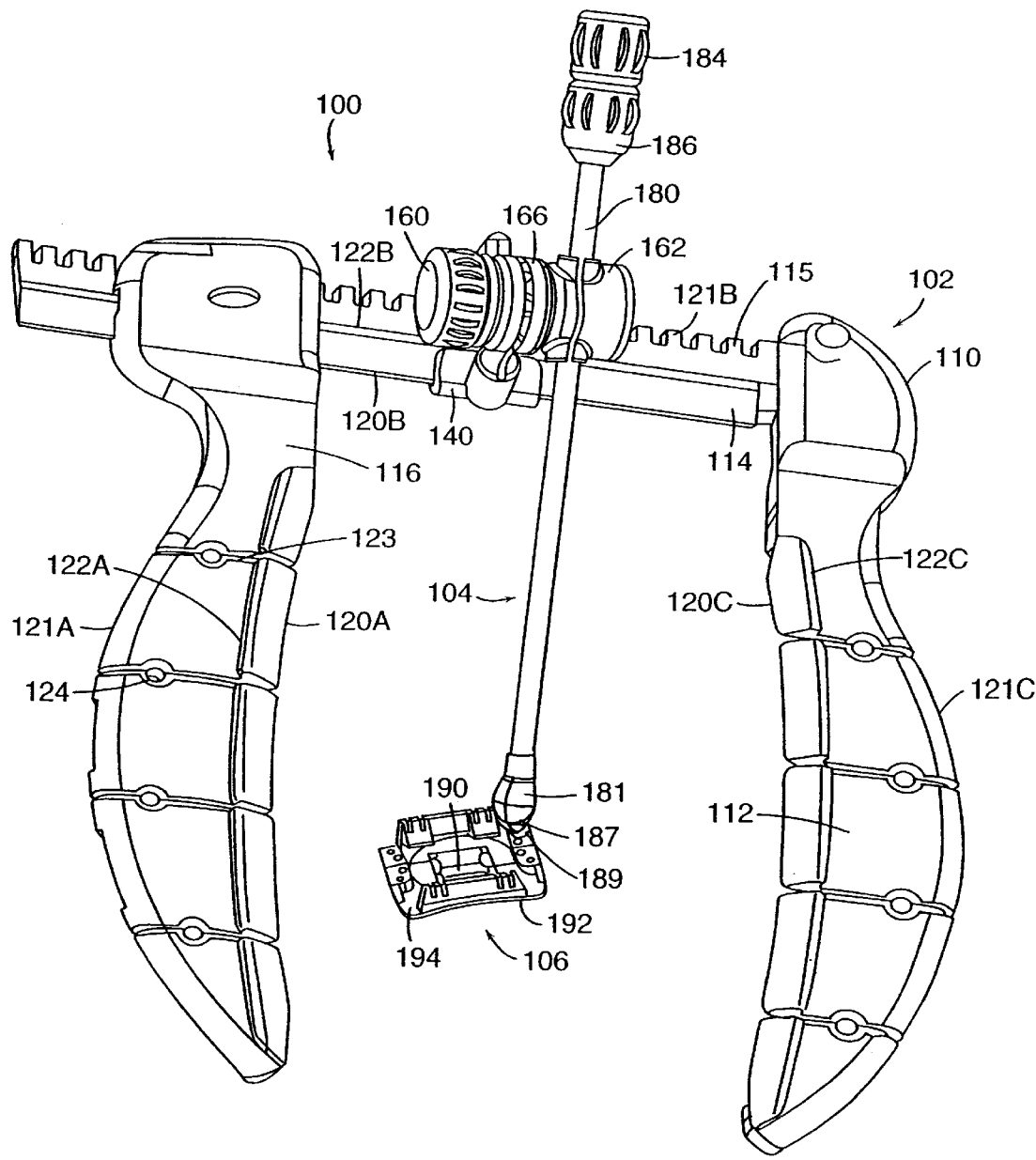
FIG. 2 is a perspective view of the stabilization system of the present invention with the handle removed for clarity and wherein the sled assembly of the stabilization system is positioned on the rack segment of the retractor.
Figure 3A:
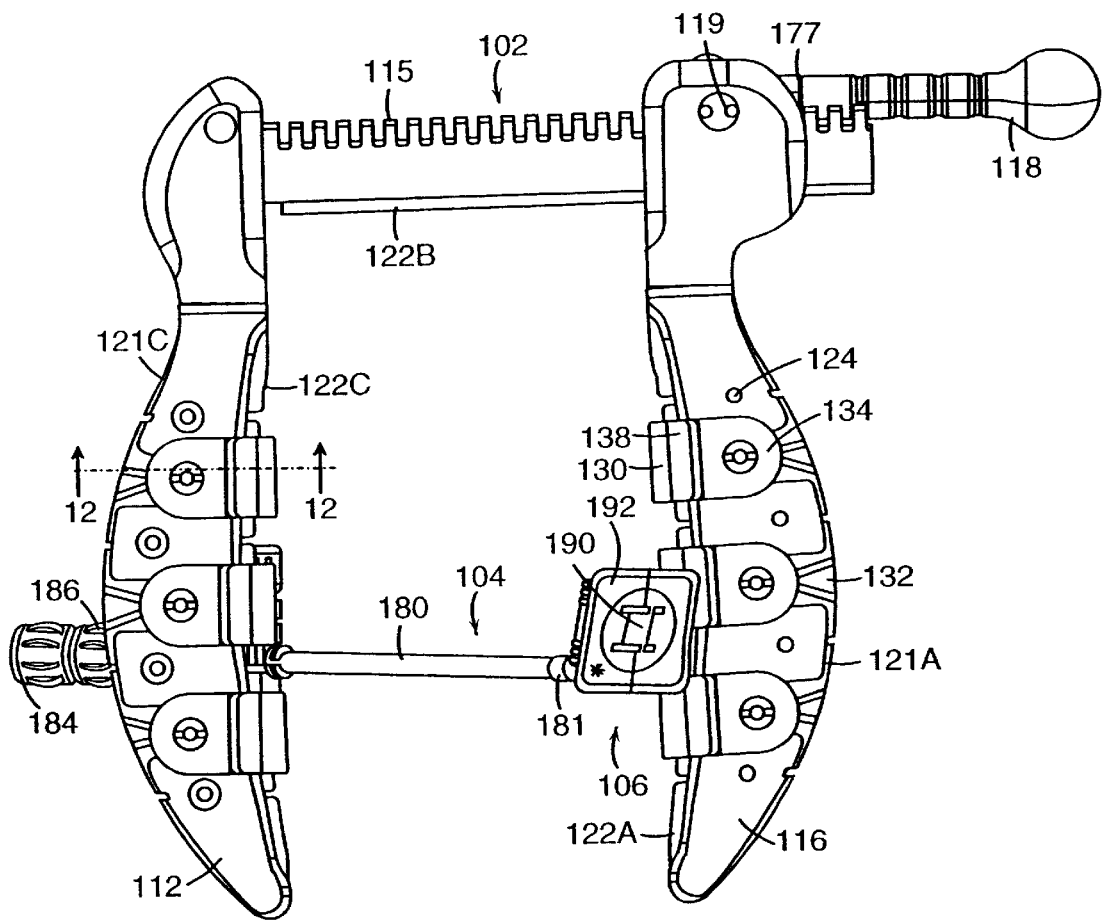
FIGS. 3A and 3B are bottom perspective and bottom isometric views of the stabilization system of FIG. 1.
Figure 3B:
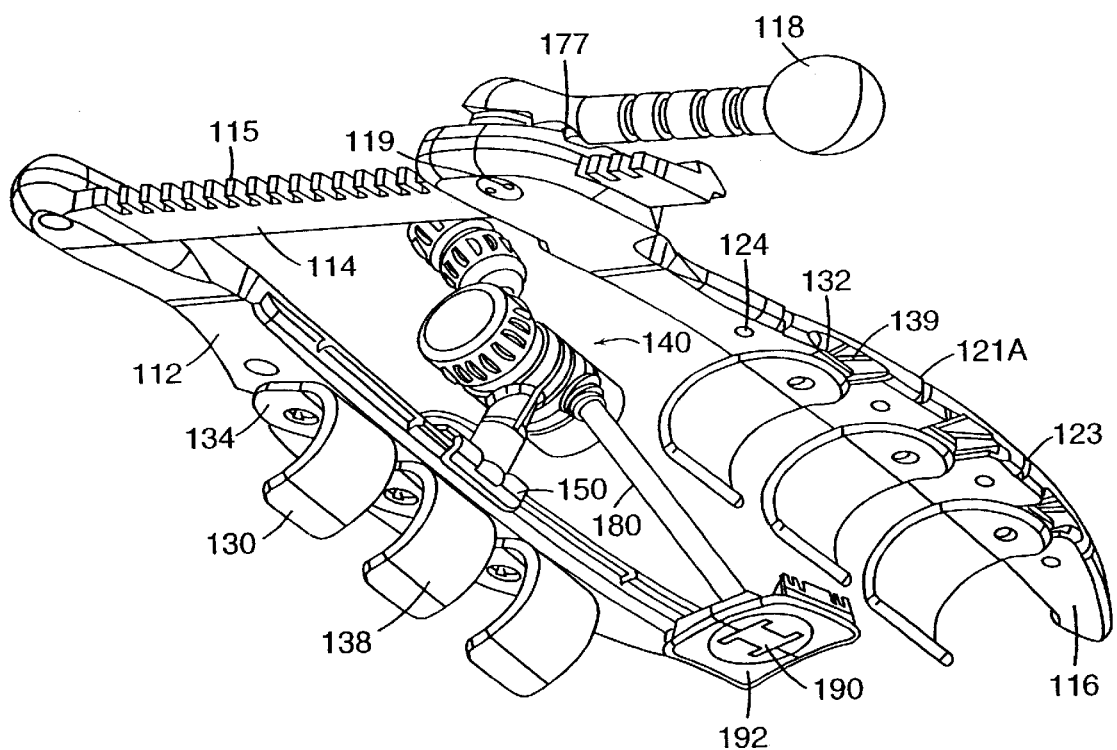
Figure 4:
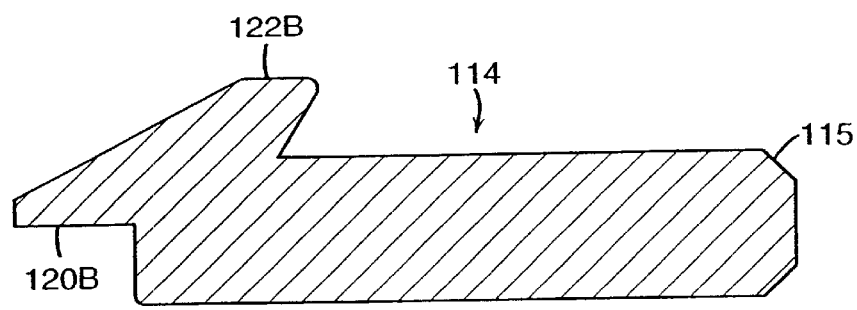
FIG. 4 is a cross sectional view of the rack segment taken generally along lines 4—4 of FIG. 1.
Figure 5:
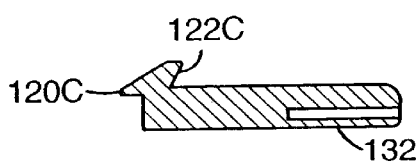
FIG. 5 is a cross sectional view of the arm section taken generally along lines 5—5 of FIG. 1.
Figure 7:
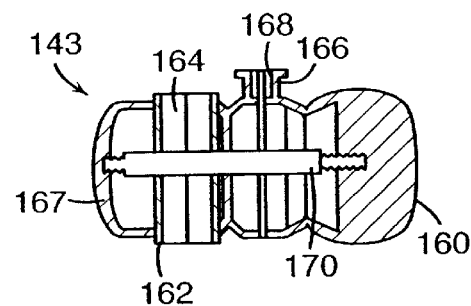
FIG. 7 is a cross-sectional view of the upper portion or mounting mechanism of the sled assembly of the stabilization arm system of the present invention taken generally along lines 7—7 of FIG. 6A.
Figure 8:
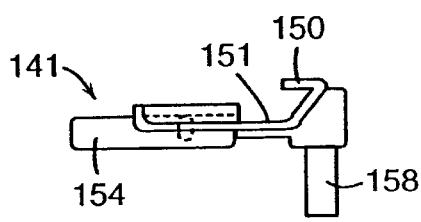
FIG. 8 is a side view of the lower portion or sled member of the sled assembly of the stabilization arm system of the present invention.
Figure 9:
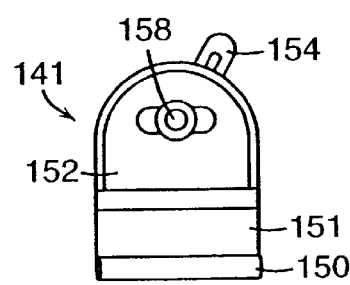
FIG. 9 is a bottom view of the lower portion or sled member of the sled assembly of the stabilization arm system of the present invention.
Figure 6A:
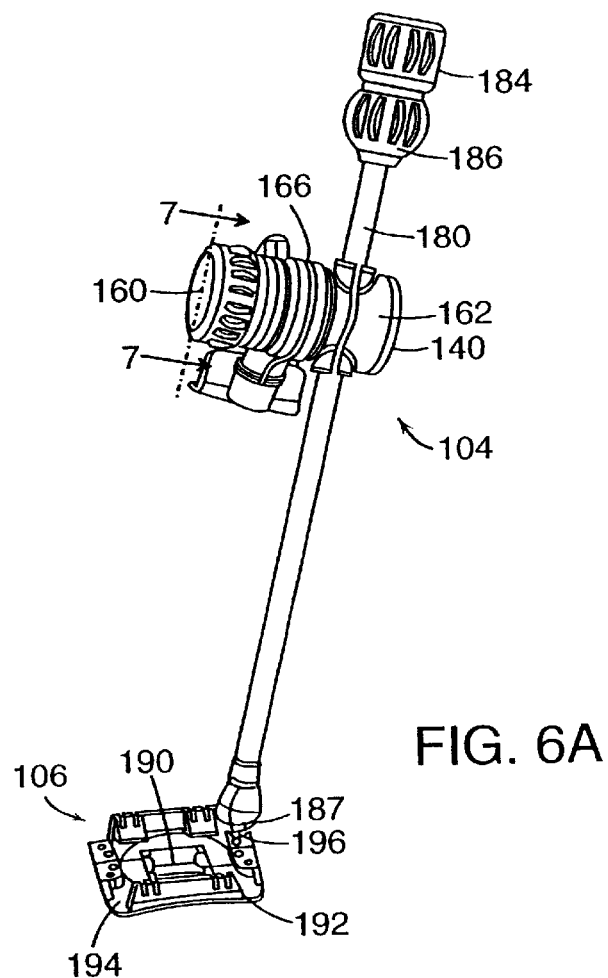
FIGS. 6A, 6B and 6C are various elevational views of the stabilization arm system and stabilization device of the present invention.
Figure 6B:
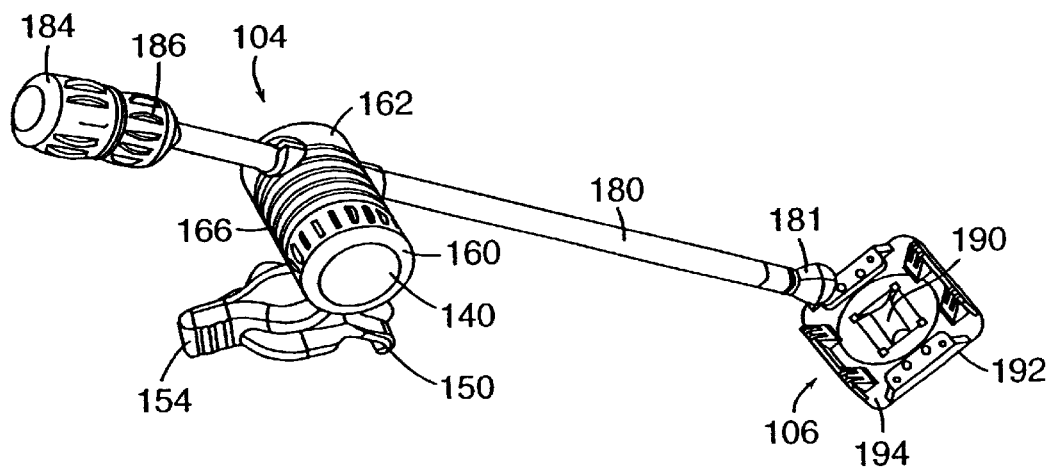
Figure 6C:
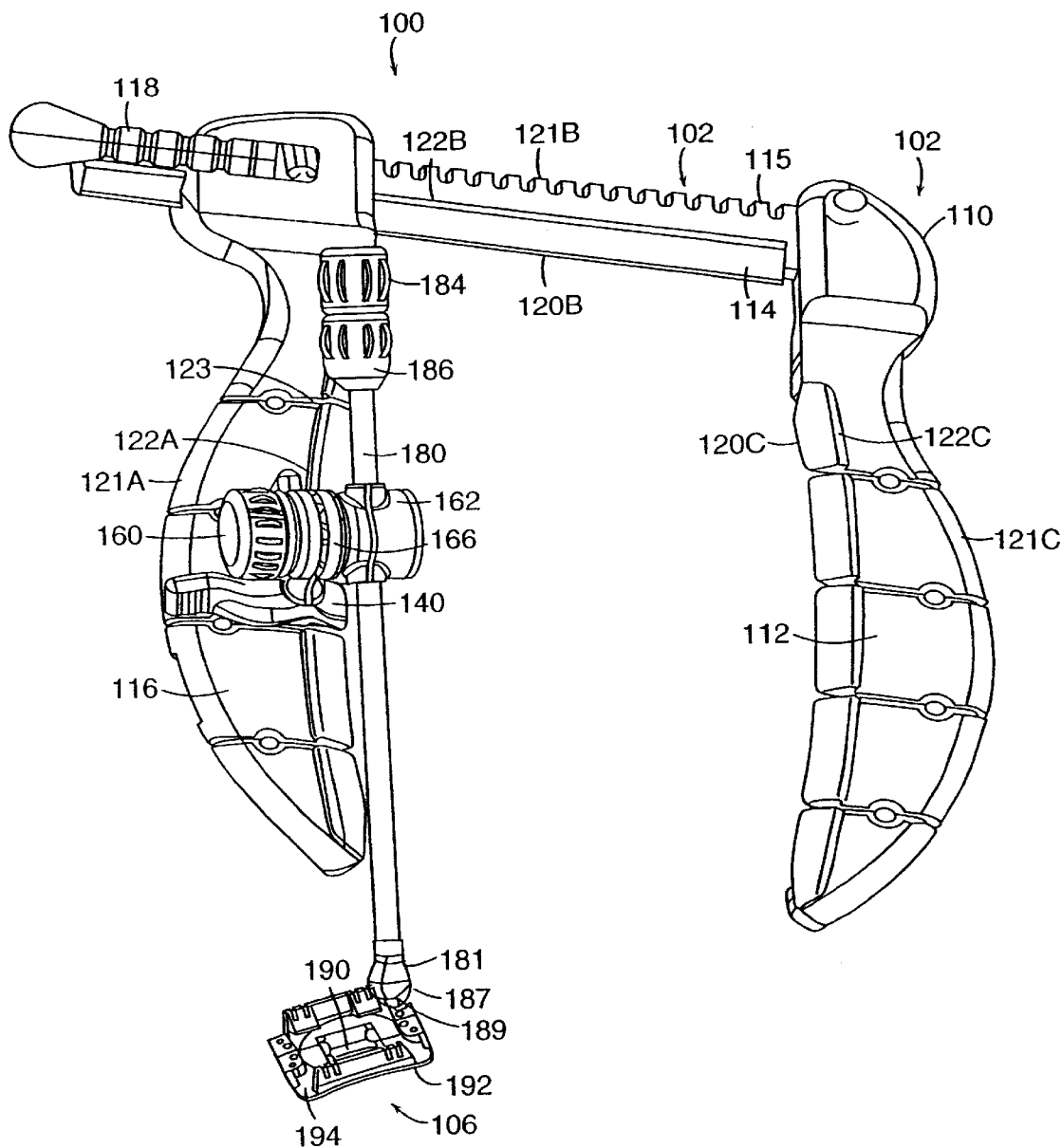
Figure 10:
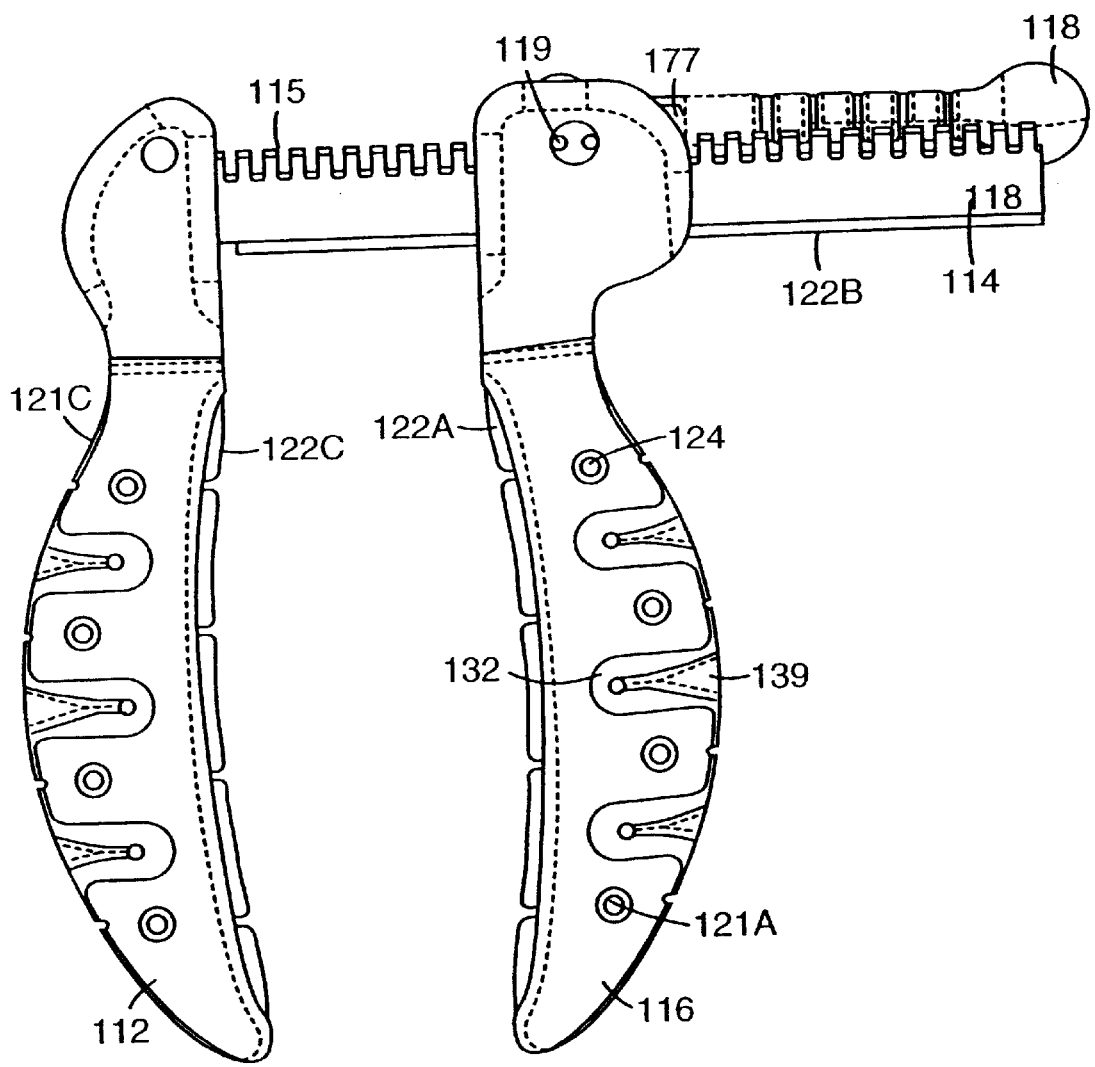
FIG. 10 is a bottom view of the retractor of the present invention with the blades removed.
Figure 11:
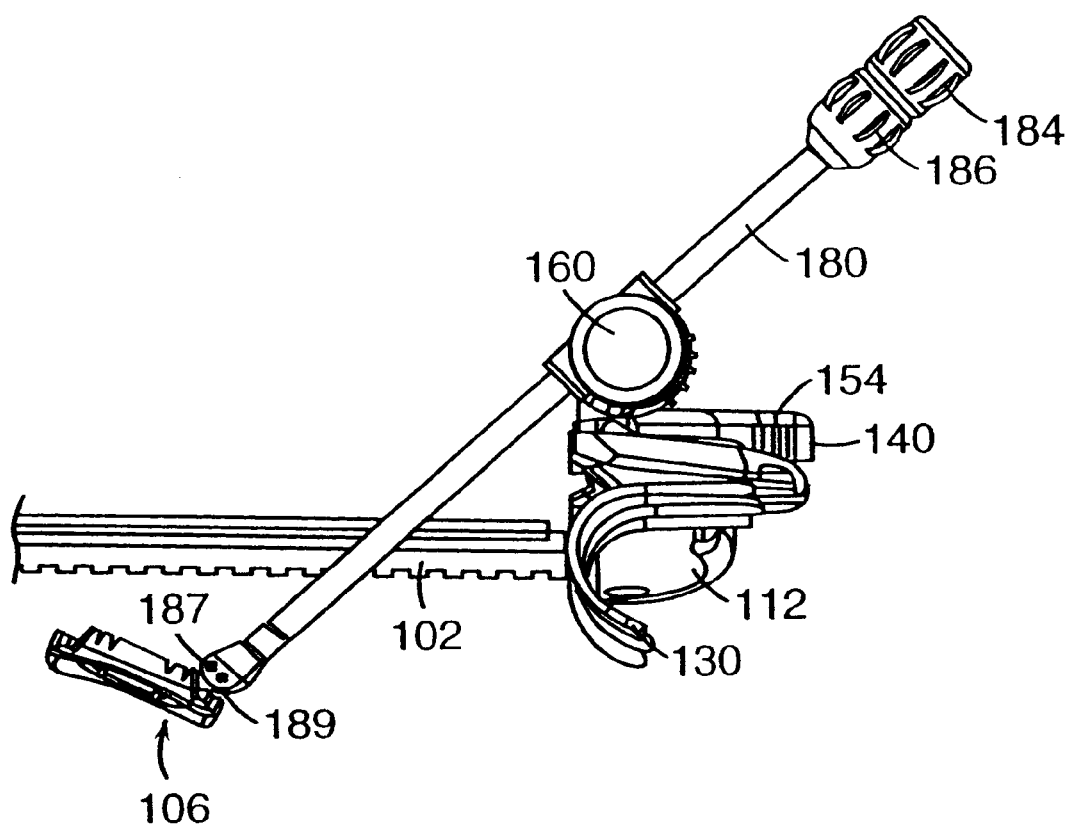
FIG. 11 is an end view of the retractor of the present invention with the blades thereon.
Figure 12:
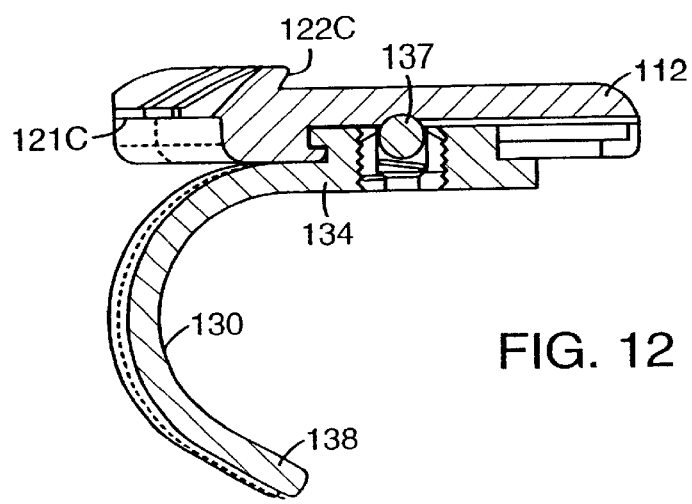
FIG. 12 is a cross sectional view taken generally along lines 12—12 of FIG. 3 with the blade inserted in the ridged slot of the arm.
Figure 13A:
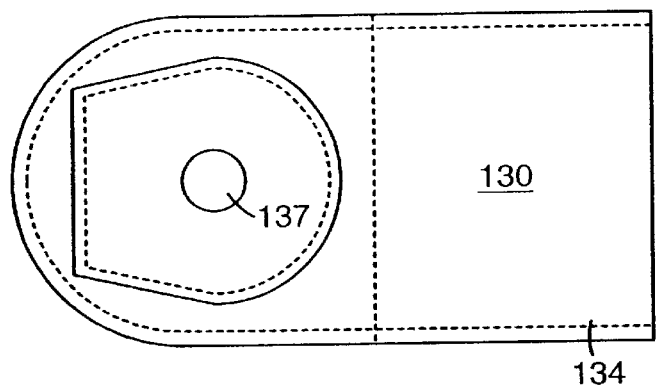
FIGS. 13A and 13B are top and bottom perspective views of the blade member of the present invention.
Figure 13B:
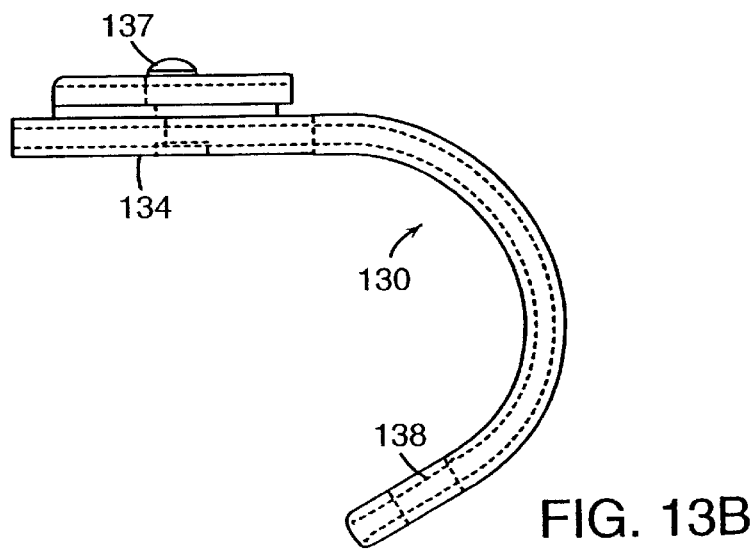

Referring now to the various figures of the drawings wherein like reference characters refer to like elements, there is shown various views of a preferred and alternate form of a stabilization system 100 according to the present invention for contributing to the stabilization of a predetermined area of a body such as the predetermined area of a heart or other organ of a patient to enable the physician to perform a surgical operation or procedure on a patient. The stabilization system 100 is particularly useful in connection with single or multiple vessel off-pump coronary artery bypass surgery on a beating heart through a sternotomy or mini-sternotomy incision.

A surgeon may use the stabilization system 100 to apply a slight contacting or compressive force on the heart in the area where the surgical procedure will occur so the heart's movement at that specific area is diminished. In a preferred form of this invention, the stabilization system 100 is used in combination with flexible tapes or sutures or other mechanical means so that the surface of the heart is stabilized using a combination of restraining and stabilizing forces. In certain procedures, it may also be advantageous to place a traction suture around an artery using a needle and suture thread to occlude the blood vessel. These sutures may then be attached to the stabilizing device so that the flow of blood through the blood vessel is selectively restricted.

Systems for stabilizing the heart of a patient are particularly useful for various heart suturing techniques or procedures. One example of this type of procedure is the performance of an anastomosis for a bypass graft. In this type of procedure, the physician is attempting to suture the circumference of a blood vessel that may be about 1 mm to a moving blood vessel on the surface of the heart. Another area of use of the present invention may be in brain surgery, heart valve surgery or other types of blood vessel surgery where stability is critically important to avoid disastrous consequences or where it is desirable to have a precisely defined surgical field. One skilled in the art will appreciate that the present invention, although advantageously suited for heart surgery, can be used at any location on or within the body where tissue stabilization or isolation of a predetermined area is desired. This includes, but is not limited to, the liver, kidneys, bladder, stomach, intestines, brain and vascular and other soft tissue surgery.

Additionally, one skilled in the art will appreciate, as hereinafter described, that the supporting components of the system can be readily adapted so that any surgical instrument or device can be self-supported during a surgical procedure. For example, it is anticipated that the sled assembly 140 described below may be used to retain nearly any medical instrument, including valve retractors, graspers etc., so that the retractor 102 operates as an operating or surgical platform from which the various instruments or devices may be attached using the sled assembly described below. This provides the user with an extremely versatile platform that may be used to grasp the handle of various instruments and allow the user to slide and rotate the instruments to their desired location along any surface of the platform and to also adjust the orientation of the instrument as desired in the manner described more fully below in the context of the use of the retractor and stabilization device.

Referring specifically to FIGS. 1–4, the stabilization system 100 according to the present invention includes a retractor 102, a stabilization sub-system or stabilization arm system 104 and a stabilization device 106. The retractor 102 is specifically configured so the stabilization arm system 104 can be secured thereto. The retractor 102, preferably includes a rigid L-shaped member 110 having an arm segment 112 and a rack segment 114. The retractor 102 also includes a movable second arm segment 116 having a handle 118 thereon which is movably associated with the L-shaped member 110.

The stabilization arm system or sub-system 104 preferably includes an elongate handle segment 180 that preferably interconnects the retractor 102 and the stabilization device 106. The handle segment 180 preferably includes a first end having a distal connector 181 thereon to pivotally and removably retain the stabilization device 106 thereon. The handle segment 180 is attachable to the retractor 102 by a connector such as a the sled assembly 140. The proximal or second end of the handle segment 180 preferably includes a knob 184 thereon that is rotatable with respect to the handle segment 180 to allow the movement of the stabilization device 106 to be pivotal and/or fixed with respect to the handle segment 180 by manipulating the knob 184 on the proximal end of the handle segment 180. This arrangement also allows the stabilization device 106 to be mountable on and removable from the distal connector 181.

The preferred form of the stabilization device 106 is generally a rectangular shape having an opening or window area 190 therein. The stabilization device 106 preferably includes a first surface 192 that is generally planar and may include a textured surface thereon to facilitate the engagement between the stabilization device and the tissue of the predetermined area or the heart of the patent. The second surface 194 of the stabilization device 106 preferably includes a post member 196 extending therefrom. The post member 196 is preferably releasably and rotatably engaged by the distal connector 181 on the first end of the handle segment 180.

As described briefly above, the retractor 102 preferably includes a handle 118 located on the second arm segment 116 and the handle 118 is rotatable for displacing the two arm segments 112,116 with respect to each other. In the preferred form of this invention, rotation of the handle 118 causes a pair of posts or pinions 119 to sequentially engage the teeth 115 located on the outer edge 121b of the rack segment 114 to increase or decrease the distance between the first and second arms 112 and 116. As shown, the handle includes a projection 177 on the bottom surface thereof which fits in a slot located in the retractor adjacent to the arm and rack segment to allow the user to lock the handle into position once the arms are in the desired position. This feature is particularly useful where the retractor is reused for a relatively long period of time for multiple procedures because the pinions and teeth on the retractor will gradually wear due to the pressure from the chest of the patient. As the wear occurs, the pressure from the sternum may cause the arms to move towards each other unless the arms or handle are retained in a locked position. In a specific illustrative embodiment, the rack segment 114 is configured with a finochetti type of rack as is known to those skilled in the art. In conjunction with the handle 118, the rack segment 114 and movable second arm 116 form a rack and pinion type of means for displacing the arm segments 112, 116 with respect to each other. As shown, this type of rack segment 114 includes a plurality of laterally extending teeth members 115 that engage the posts 119 or similar tooth engaging members located in operative contact with the handle 118 of the second arm segment 116.

It is anticipated that a variety of mechanisms may be used to move the second arm segment 116 along the rack segment 114. For example, a gear mechanism, a slide and locking mechanism or similar arrangement may be used to accomplish the separation and fixation of the second arm 116 with respect to the first arm 112. It is within the scope of the present invention, however, for the retractor 102 to be configured or designed with any of a number of means known to those skilled in the art for selectively displacing the first and second arm segments, 112 and 116 either towards or away from each other in a parallel, obtuse or acute angled manner.

At least one arm segment and preferably each arm segment, 112 and 116 respectively, and the rack segment 114 are configured so as to each have a front edge surface 120a, 120b and 120c extending along the inner surface of each element of the retractor 102 such that the front edges of each of the arms and the rack segment face each other. The retractor 102 also preferably includes an outer edge surface 121a, 121b and 121c extending along the outer surface of the first and second arms, 112 and 116 respectively, of the retractor 102. A step surface 122a, 122b and 122c extends along the top surface of the first and second arms, 112 and 116 respectively, and the rack segment 114 in a spaced apart relationship with respect to the front edges of each of the surfaces of the first and second arms and the rack segment to form an elongate lip or external rail surface on the arms and rack segment of the retractor. The step surfaces 122a–c are preferably located a preset distance back from the front edge and forms an acute angle facing away from the front edge thereof on each of the arms and the rack segment. As described hereinafter, the front edge surfaces 120a–c and the step surfaces 122a–c on the top surface of the arms and rack segment are particularly arranged and configured to face each other and so that the sled assembly 140 can be readily secured to the retractor 102 by engaging the front edge surface (120a, 120b or 120c) and the associated step surface (122a, 122b or 122c) on each of the first and second arms, 112 and 116, and the rack segment 114.

As also shown in the top views of the preferred form of the present invention, the front edge surfaces 120a and 120c of the first and second arm segments that are adjacent to the step surfaces 122a and 122c are of a preferably slightly concave orientation such that the mid point of the first and second arms are spaced apart from each other a greater distance than the distance of either or both of the inner or outer ends of the first and second arms, 112 and 116. Additionally, the outer edge surfaces 121a and 121c of each arm preferably has a greater curvature than the front edge surfaces 120a and 120c of the same arm so that as the retractor 102 spreads the chest of the patient, the motion of separating the first and second arms, 112 and 116, is emphasized to increase the amount the chest of the patient is spread. Therefore, at a given distance of separation between the first and second arms, 112 and 116, the midpoints of the outer surface of the arms will be separated a further distance than at the ends adjacent to the rack segment or at the ends furthest from the rack segment 114 due to the overall generally clam-shell shaped configuration of the preferred form of the present invention. An advantage of this configuration is that the surgeon is provided with an opening in the sternum of the patient that is wider in the center than along the edges so that the most common area of work for the surgeon is larger than a conventional retractor for the same amount of separation.

Additionally, as shown in the drawings, the top surface of each of the arms, 112 and 116, preferably include a plurality of slots 123 extending generally perpendicular to the lengthwise dimension of each arm. These slots 123 extend from the front edge surfaces 120a and 120c; through the step surfaces 122a and 122c; and to the outer edge surfaces 121a and 121c, respectively on each of the first and second arms, 112 and 116. These slots 123 are configured to extend through the front edge surface 120a and 120c of each arm, 112 and 116, to allow the sled assembly 140 to be moved therealong while not cutting or interfering with any sutures that may be positioned in the slots. Additionally, each of the slots 123 preferably include a through hole 124 in communication with the slot and extending through the arm. In the preferred use of the present invention, the slots 123 are preferably used to position sutures that have been threaded through the pericardium of the patient therein so that the pericardium or other tissue is retracted and held out of the line of sight of the surgeon by the sutures to better expose the heart of the patient. With the preferred form of the present invention, the sutures and clamps are retained out of the working area of the surgeon. The portion of the through hole 124 adjacent to the top and bottom surfaces of the arm are preferably tapered so that the distal end of the clamps or other instruments that are used to hold the sutures may be placed and retained therein during the procedure. By allowing the distal ends of the instruments to be placed into the through holes 124, the sutures are held in a secure position during the procedure and may be adjusted as needed at any time by lifting the instrument and then reclamping the suture or releasing the clamp and then pulling the suture through the clamp and subsequently closing the clamp while it remains in the through hole. Additionally, it is anticipated that some surgeons may use these through holes to suture the retractor to the patient to minimize possible extraneous movement of the retractor during the procedure.

In an exemplary embodiment of the present invention, the bottom surface of each of the first and second arms, 112 and 116, on the retractor 102 include removable sternal blades 130 attached thereto. Each blade 130 is removable so as to facilitate the use of the retractor in a full or mini-sternotomy procedure by allowing for the selective positioning and spacing of the blades 130 as desired for the particular procedure as well as for resterilization of the retractor 102 and blades 130. As illustrated, the blades 130 are positioned along the bottom surface of the arms 112 and 116 and are preferably pivotal in the horizontal and vertical directions with respect to the arms. The blades 130 are slidable into elongate ridged slots 132 on the bottom surface of the first and second arms, 112 and 116. The blades 130 may swivel a limited distance and are selectively positioned in the slots 132 so as to evenly distribute the retraction forces or pressure along the contour of the sternum of the patient.

An upper section 134 of each blade 130 is particularly configured to facilitate the insertion of the blades into the retractor. In particular, the upper section 134 of the blade 130 is configured so that an upward extending and generally oblong shaped lip member 136 is received in the ridged slots 132 located on the bottom surface of the first and second arms, 112 and 116. This surface further includes a raised ball member 137 which slides in a further slot 139 located in the ridged slots. The ball member is slightly depressible so that it may be slid beyond the further slot 139 so that during the initial placement of the retractor, the blades may be positioned to extend nearly linearly along each arm in an insertion position. As the arms are retracted, the inner and outermost blades move to a retraction position to assume a slightly curved shape. In the preferred form of the present invention, the retraction position generally approximates the anatomy of the patient and allows the pressure of the sternum of the patient to be evenly distributed among the blades. The use of the ball member and the further slots and the ridged slots allow the blades to temporarily assume the linear configuration and also rise slightly to provide a lower profile and maintain the retraction edge. Once the blades are inserted into the sternum, the slight release of the pressure during the insertion allows the ball member to return to the innermost end of the further slot and the blades may pivot slightly in the vertical and horizontal directions so that the blades follow the slightly curved shape of the retraction position and provide optimum leverage to retract the sternum of the patient.

The upper section 134 of the blade 130 extends generally along the bottom surface of the first and second arms, 112 and 116 and is positioned so the blade 130 extends a short distance inwardly of the front edge surfaces 120*a* and 120*c* of the arms 112 and 116. The blades 130 also include a lower section 138 which extends downwardly from the upper section 134 of the blade 130 in a curved manner to extend beneath the bottom surface of the retractor to readily engage the sternum of the patient. The lower section also preferably curves backward a short distance towards the outer edge surface 121 of the first and second arms, 112 and 116, to form a blade 130 having an overall C or L shape that facilitates the positioning and retention of the sternum of the patient adjacent thereto. Therefore, the blades 130 in conjunction with the displacement of the first and second arms result in the desired retraction of the tissue, bone etc. for the surgical procedure.

The stabilization sub-system or stabilization arm system 104 of the present invention preferably includes an elongate handle segment 180 that interacts with the retractor 102 and the stabilization device 106. The handle segment 180 is preferably a rigid tubular member that includes a distal connector 181 on the distal end thereof to pivotally and removably retain the stabilization device 106 thereon. The handle segment 180 is attachable to the retractor 102 by a connector such as a sled assembly 140. The proximal end of the handle segment 180 preferably includes a movable knob 184 and a fixed knob 186 thereon. The movable knob 184 is connected to an elongate rod that is threaded through the handle segment 180 and extends to the distal connector 181. The fixed knob 186 is fixed proximally of the movable knob 184 on the handle segment 180 to allow the user to rotate the stabilization device 106 by manipulating this fixed knob 186 when the stabilization device 106 is connected to the distal connector 181 of the handle segment 180.

As illustrated, the distal connector 181 consists of a generally bulbous member having an elongate slot 187 extending through at least one side thereof. The slot 187 is sized to allow the post member 196 of the stabilization device 106 to pass laterally therethrough to allow the stabilization device to be easily mounted on or removed from the stabilization arm system 104. Additionally, the use of the bulbous shape on the post member 196 and the complementary shape of the slot 187 allows the stabilization device to be pivotal and rotatable about the handle segment to enable the surgeon to position the stabilization device 106 in the desired position and against nearly any surface of the heart of the patient. The stabilization device 106 is fixed in the desired position relative to the handle segment 180 by rotating the movable knob 184 with respect to the handle segment and/or the fixed knob so that a portion of the elongate rod moves with respect to the outer surface of the handle segment 180 and extends into the distal connector 181 to contact and engage the post member 196 of the stabilization device 104. This movement of the elongate rod with respect to the distal connector causes the post member to press against the lower lip surfaces 189 of the distal connector. The preferred, generally pear-like, shape of the distal connector 181 optimizes the connection between the distal connector 181 and the post member 196 to enable the stabilization device 106 to be selectively retained within the distal connector 181 while allowing for the pivotal and rotational movement necessary for the use of this device in a cardiac application where space is at a premium and the device must be as versatile as possible to accommodate the surgeons needs without undue experimentation.

The stabilization arm system 104 of the preferred embodiment also includes the sled assembly 140 operatively connected thereto. The sled assembly 140 is configured so the surgeon has multiple axis or three dimensional positioning capability for the stabilization device 106 while requiring a minimum of manipulation. In an exemplary embodiment, the lower portion of the sled assembly 140 has a sled member 141 that includes a front edge lip 150, a movable second lip 152 and an actuator lever 154. The actuator lever 154 is pivotally connected to an elongate slot in the second lip 152 by a pin 158 which is preferably offset with respect to the axis of rotation of the actuator lever 154 so that movement of the actuator lever 154 causes the second lip 152 to move towards and away from the front edge lip 150. The front edge lip 150 is configured so that the interior of this lip conforms generally to the shape and configuration of any of the retractor front edge surfaces 120*a–c*. The front edge lip 150 also includes a portion that extends backwards under the front edge surfaces 120*a–c* of the arms and/or rack segment of the retractor so the front edge lip 150 preferably forms an acutely angled surface that is easily secured at any location on any of the front edge surfaces 120*a*, 120*b* or 120*c* of the retractor 102.

As also shown in the drawings, the second lip 152 of the sled member 141 is a semicircular or oblong shaped member that is disposed in the bottom portion of the sled assembly 140 a distance back from the front edge lip to selectively engage the recessed side of any of the step surfaces 122*a–c* of the retractor. The second lip 152 also is generally configured so the inside interior surface 151 of the sled member 141 extends arcuately across and lies upon the top surface of the retractor 102 between a front edge surface 120*a–c* and the associated step surface 122*a–c* of the retractor. The second lip 152 is slidably mounted on the bottom side of the sled member 141 and is movable in response to rotation of the actuator lever 154 to form an acute step surface engaging angle between the sled second lip 152 and the inside interior surface 151 to securely retain the selected step surface 120*a*, 120*b* or 120*c* therein.

One skilled in the art would recognize that there are a number of means available in the art for removably securing the sled assembly 140 to the front edge surface and step surface 122*a–c* of the retractor. For example a wing nut or similar threaded type of arrangement where the wing nut would act on the vertical surface of the retractor step may be used. However, the use of the actuator lever 154 of the preferred embodiment provides the surgeon with a quick and simple means for attaching the sled assembly 140 to any desired location on the retractor 102 with a single handed operation of the actuator lever 154. Additionally, the distance of travel of the actuator lever 154 is chosen so as to be preferably less than about 180 degrees to further facilitate the single handed attachment of the sled member 141 of the sled assembly 140 to the retractor 102. Additionally, the actuator lever 154 is preferably positioned on the side of the sled member 141 which is adjacent to the outer edge surfaces 121*a–c* of the retractor 102 so as to not interfere with the operative field or vision of the surgeon.

In an alternate embodiment, a cam shaped member may be located on the bottom surface of the sled member instead of the second lip 152 described above. The cam shaped member may be formed as a generally circular member that is configured with a flat region on at least one part of the circumference. To place the sled assembly onto the retractor of this embodiment, the actuator lever may be rotated so that cam is rotated and the flat side of the cam faces the sled front edge lip. After the sled member of the sled assembly is placed on the retractor, the actuator lever is again rotated so the curved portion of the cam will come into contact with and engage the vertical surface of the retractor steps.

As indicated above, rotation of the cam may be accomplished by rotation of the actuator lever and the actuator lever is movable between various positions wherein the cam is fully contacting, partially contacting or spaced apart from the top surface and step of the retractor. It is within the scope of the present invention, however, for the cam to be spring loaded such that the cam automatically rotates so the curved portion of the cam contacts the retractor step when the actuator lever is not being held by the surgeon. In other words, the cam may be biased so that the curved portion of the cam faces the sled front edge lip.

It is within the scope of the present invention for the cam or second lip to have any geometric configuration or shape consistent with the preferred features of the present invention, for example, some of these preferred features relate to the ease and versatility of removably mounting the 141 onto and removing the sled assembly 140 from the retractor 102. For example, directly mounting and directly removing the sled member without being required to slide the sled member 141 on and off the ends of the arms of the retractor 102 as well as for providing the ability to mount the sled assembly 140 onto the rack segment 114 of the retractor. Furthermore, the ability to mount the sled assembly 140 on any one of the arms and rack segment on a temporary basis and then being able to slide the sled assembly into the final desired position is an advantage over the currently available retractors. This is particularly true in the preferred form of the present invention where, in the midway position of the actuator, the actuator lever will cause the retention of the sled member on the retractor while allowing sliding movement therebetween. The actuator lever may then be moved to the engaged position to lock the sled member 141 and therefore, the sled assembly 140 of the stabilization arm system 104 in the desired position on the retractor.

In the preferred embodiment of the present invention, the sled assembly 140 also includes an upper portion or mounting mechanism 143 that preferably includes a knob 160, a stabilization arm clamp 162, a sled pin clamp 166, and a threaded rod 170 therein. The mounting mechanism 143 portion of the sled member 140 provide the surgeon with the rotational movement of the stabilization arm system 104 in a combination of horizontal and vertical directions as well as allowing for the sliding and rotational movement of the handle segment 180 therethrough, all of which are advantageously controlled by the operation of the single knob 160 that is located along the periphery of the operative field and which improve the ability of the surgeon to position the stabilization device 106 in the desired position.

The sled pin 158 extends upwardly from the sled member 141 of the of the sled assembly 140 to form a first or horizontal axis of rotation between the sled member of the sled assembly that includes the front edge lip 150, second lip 152 and the actuator lever 154 described above and the mounting mechanism 143 of the sled assembly as described below. As shown, the sled pin 158 is also preferably offset from the axis formed by the knob and threaded rod of the upper portion to allow the mounting mechanism 143 of the sled assembly 140 to be rotated about the sled member 141 of the sled assembly 140 so that the handle segment is movable relative to the front edge surfaces of the retractor as desired by the surgeon. This arrangement also enables the sled member of the sled assembly to be rotatable with respect to the mounting mechanism 143 of the sled assembly 140 independently of whether or not the sled member 141 is locked into position along the arms and/or rack segment of the retractor. Furthermore, this arrangement enables the sled assembly to be movable along the retractor independently of whether or not the sled member is locked into position relative to the mounting mechanism of the sled assembly. Additionally, this orientation allows the mounting mechanism of the sled assembly to be preferably positioned directly above the front edge of the retractor as shown and significantly increases the range of motion of the sled assembly and therefore the range of motion of the stabilization arm and ultimately significantly increases the versatility and range of motion for positioning the stabilization device. For example, rotation of the mounting mechanism 143 of the sled assembly 140 and stabilization arm system 104 will allow the user to position the aperture inwardly of the front edge surfaces of the retractor so that the stabilization device 106 may be positioned beneath the arms and/or rack segment. This orientation is particularly useful in situations where the posterior surface of the heart is being operated on as well as in certain situations where the selected portion of the heart is manipulated to a side of the operative field. This type of orientation may require the handle segment to be oriented at an angle which is generally greater than perpendicular to the width dimension of the arms or rack segment. Alternately, the sled pin may be oriented at an acute angle relative to the horizontal surface of the retractor to cause the mounting mechanism of the sled assembly to extend inwardly of the front edges of the arms and rack segment to further increase the versatility of the present invention by providing a lower profile approach to the desired location in the patient.

The sled pin 158 is rotatably received in a recess or pocket 168 that is formed in left and right sections of the sled pin clamp 166 on the mounting mechanism 143 of the sled assembly 140. In the preferred form of the present invention, the pocket may include a separate metal clamp member that is fixedly positioned in the pocket and is compressible in response to movement of the knob 160. The addition of the separate clamp member in the pocket 168 provides a further gripping surface that enables the sled pin and sled pin clamp to fixedly engage each other when the knob is rotated, thereby retaining the stabilization device in the desired position once the surgeon rotates the knob 160. In this way, and as described hereinafter, the mounting mechanism 143 can be rotated horizontally relative to the retractor by the surgeon about the sled pin 158 to facilitate the secure rotational positioning of the stabilization arm system 104 and stabilization device 106 at the desired predetermined area on the heart of the patient as well as to move the handle segment closer to or further from the front edge surfaces of the retractor.

The left and right sections of the stabilization arm clamp 162 on the mounting mechanism 143 are configured so as to form a through aperture 164 therein. This aperture 164 is preferably offset from the rotational or horizontal axis of the knob 160 and threaded rod 170 to increase or decrease height of the aperture relative to the retractor thereby changing the angle of approach of the handle segment 180 to the operative field. As shown, the preferred configuration orients the aperture 164 above the rotational axis of the knob 160. If desired by the surgeon, the aperture 164 and therefore the handle segment 180 may be positioned below the rotational axis of the knob so that the handle segment will approach the operative field at a lower angle. The aperture 164 slidably and rotationally receives the handle segment 180 of the stabilization arm system 104 therein. The stabilization arm clamp 162 is rotatably disposed about the threaded rod 170 to allow the handle segment to be rotatable in a vertical direction relative to the retractor. Therefore, the preferred form of the stabilization arm clamp is movable about the longitudinal axis of the threaded rod 170 as well as being separately rotatable and slidable with respect to the aperture 164. The rotational surfaces between the stabilization arm clamp 162 and the sled pin clamp 166 may also preferably have a plurality of complementary ridges and valleys thereon so as to form a poker chip type surface on each of these surfaces of the clamps. The use of this type of surface preferably allows the vertical rotation of the handle segment relative to the retractor. This arrangement also limits the rotational movement of the stabilization arm clamp 162 with respect to the sled pin clamp 166 when the knob 160 and threaded rod 170 are intermediately or fully tightened by providing an additional source of friction that must be overcome to rotate the handle segment with respect to the stabilization arm clamp 162 and sled pin clamp. Additionally, the use of this type of surface between the clamps, facilitates the fine positioning of the stabilization device 106 by preventing the rotational movement of the stabilization arm clamp 162 while the surgeon is still able to overcome the frictional resistance to the rotational and sliding movement the handle segment 180 when the knob 160 is not fully tightened.

The preferred form of the present invention also includes the threaded rod 170 that is fixedly attached to the knob 160 and extends between the knob 160 and the outer section 167 of the sled pin clamp 166 on the mounting mechanism 143. In this way, and as described hereinafter, the stabilization arm clamp 162 and thus the handle segment 180 of the stabilization arm system 104 can be rotated by the surgeon about the threaded rod 170 prior to the knob 160 being rotated to a fully engaged position wherein relative movement is prevented. Additionally, the handle segment 180 may also slide and/or be rotated with respect to the stabilization arm clamp 162 through the aperture 164 to facilitate positioning of the stabilization device 106 through the manipulation of an actuation member such as the single knob described herein or through a single lever or handle.

The knob 160 is secured to one end of the threaded rod 170 and the other end of the rod engages the outer section 167 of the sled pin clamp 166. The sled pin clamp 166 and the stabilization arm clamp 162 are each located offset from and rotationally about the threaded rod 170. The rotation of the knob 160 in one direction (e.g., clockwise direction) moves the left and right sections of each of these clamps towards each other (i.e., compresses the clamps) so as to clamp onto each of the sled pin 158 and the handle segment 180 respectively. The compression of the sled pin 158 by the sled pin clamp 166 limits the rotational movement of the sled member 141 of the sled assembly 140 with respect to the mounting mechanism 143 of the sled member 140 thereby limiting the generally horizontal movement of the stabilization arm system 104 with respect to the retractor 102. The compression of the handle segment 180 by the stabilization arm clamp 162 prevents the rotational and sliding movement of the handle segment 180 through the aperture 164 and therefore causes the stabilization device 106 to be held in a fixed position relative to the sled assembly 140 and the retractor 102.

Similarly, rotational movement between the stabilization arm clamp 162 and the sled pin clamp 166 is limited by tightening the knob 160 to a fully engaged position to limit the generally vertical rotation and up or down movement of the stabilization arm system 104 with respect to the retractor 102. Rotation of the knob in the opposite direction (e.g., counterclockwise direction) causes each of these clamps 162 and 166 to separate and enable the clamps to be rotatable about the sled pin 158 and/or the threaded rod 170. In the preferred form of the present invention, each of the clamps are biased in the open position to facilitate the separation of the clamps as the knob is rotated in this position although other predisposed positions may be utilized. Additionally, the handle segment 180 may slide and rotate within the stabilizer arm clamp 162 and through the aperture 164. As one skilled in the art would appreciate, the knob 160 may be rotated in the direction of clamping so as to increase the resistance of rotation about the sled pin 158 and to increase the resistance to sliding and/or rotation of the handle segment 180 in the aperture, without completely preventing such rotation and/or sliding. This may be done to facilitate the precise positioning of the stabilization device 106 by the surgeon. Additionally, the clamps 162 and 166 may be arranged so that the initial rotation of the knob 184 may first allow horizontal movement, vertical movement or release of the handle segment 180 prior to the release of the sled pin 158, sled pin clamp/stabilization clamp interface or the handle segment 180 as desired. For example, the clamps 162 and 166 may be arranged to initially allow for or prevent the rotation of the stabilization arm clamp 162 relative to the sled pin clamp 166. Thereafter, the clamps 162 or 166 may release the sled pin 158 and handle segment 180 at the same time or sequentially. Although the preferred form of the present invention is described herein as a knob, it is anticipated that a lever or similar actuation member may be used to accomplish the desired, orientation of the stabilization device 106 relative to the retractor 102. Additionally, the preferred form of the present invention consists generally of the knob, the sled pin clamp and then the stabilization clamp. It is anticipated that this order may be adjusted such that the knob is centrally located or the stabilization clamp is located adjacent to the knob with the sled pin clamp being spaced apart therefrom. Additionally, the use of the sled assembly having the mounting mechanism and sled member may be modified to provide a single member or a different combination of rotational movements between the components.

Figure 14B:
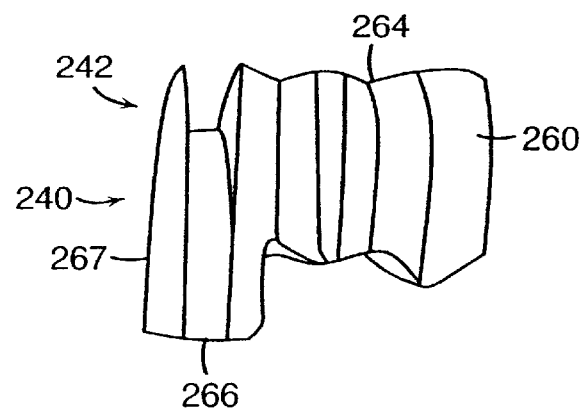
FIG. 14B is a perspective view of the upper portion of the sled assembly showing the mounting mechanism of the embodiment of the sled assembly of FIG. 14A without the sled member for clarity.
Figure 14A:
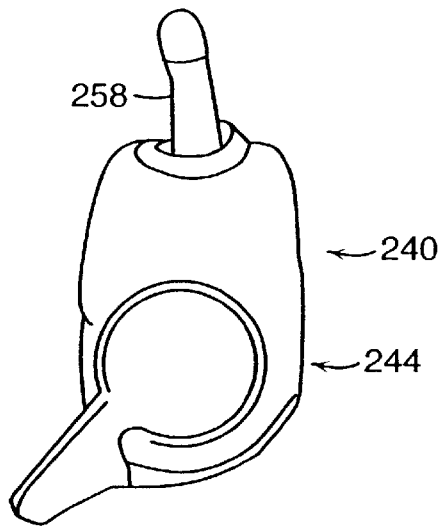
FIG. 14A is a perspective view of the lower portion of the sled assembly showing the sled member of an alternate embodiment of the present invention.
Figure 14C:
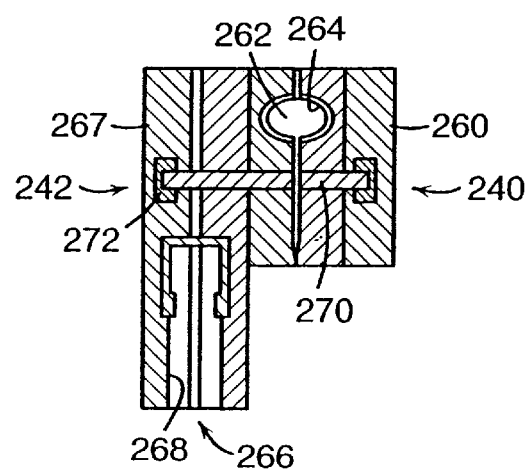
FIG. 14C is a cross-sectional view of the mounting mechanism of the sled assembly of FIG. 14B.

FIGS. 14A, 14B and 14C are illustrative of an alternate form of the sled assembly 240 of the present invention having the mounting mechanism 242 and the sled member 244 as described herein. The mounting mechanism 242 of the sled assembly 240 of this embodiment preferably includes a knob 260, a stabilizer arm clamp 262, a sled pin clamp 266 and a threaded rod 270. The sled pin 258 on the sled member 244 of this embodiment is rotatably received in a pocket 268 that is formed in the right and left sections of the sled pin clamp 266 on the mounting mechanism 242 of the sled assembly 240. In this way, and as described previously, the mounting mechanism 242 of the sled assembly may be rotated by the surgeon about the sled pin to facilitate the positioning of the stabilization device at the desired location on the patient.

The left and right sections of the stabilizer arm clamp 262 are configured so as to form a through aperture 264 that slidably receives a portion of the handle segment 180 therein. The stabilizer arm clamp 262, as shown in FIG. 14C, is offset and rotatably disposed about the threaded rod 270. The threaded rod 270 extends between the knob 260 and the outer section 267 of the sled pin clamp 266. In this way, the handle segment can slide within the stabilizer arm clamp 262 through the aperture 264 to facilitate positioning of the stabilization device in the desired orientation and location adjacent to the desired tissue of the patient. Additionally, in this embodiment, the stabilizer arm clamp 262 is positioned adjacent to the knob 260 as compared to the prior embodiment wherein the sled pin clamp 166 was positioned adjacent to the knob 160. This orientation in the present embodiment allows for a rotational movement of the handle segment relative to the retractor and sled pin that is different from the rotational movement as described above with the prior embodiment.

The knob 260 of the present embodiment is secured to one end of the threaded rod 270 and the other end of the rod threadedly engages the threaded aperture in a bushing 272 that is secured to the outer section 267 of the sled pin clamp 266. As also shown in FIG. 14C, each of the sled pin clamp 266 and the stabilizer arm clamp 262 are located adjacent to and offset from the threaded rod and between the outer section 267 and the knob 260. Thus, rotation of the knob 260 in one direction (e.g., clockwise direction) moves the left and right sections of each of these clamps towards each other (i.e., compresses the clamps) so as to clamp onto each of the sled pin 258 and the handle segment so the stabilization device is retained in a fixed position relative to the retractor. Correspondingly, rotation of the knob in the opposite direction (e.g., counterclockwise direction) causes each of these clamps 262 and 266 to release due to the preferred opening bias of the clamps. Therefore, the mounting mechanism of the sled assembly may be rotated about the sled pin and the handle segment may be moved relative to the aperture and/or the threaded rod as desired by the surgeon. The operation and structure of the sled member 244 of this embodiment is similar to the operation and structure of the sled member of the prior embodiment and therefore, for the sake of brevity, will not be repeated at this time and reference should be made to the discussion set forth above.

The use of the stabilization system 100 according to the preferred aspect of the present invention can be best understood from the following discussion with reference to the drawings. Although the following discussion makes reference to the use of the stabilization system specifically in connection with a coronary artery bypass grafting surgical procedure, the use of the stabilization system of the present invention is not limited to such uses.

After appropriately preparing and positioning the patient for the surgical procedure and completing those actions required in advance of the use of the stabilization system, the arms 112 and 116 of the retractor 102 would be closed such that the upper portion 134 of the blades 130 are generally abutting each other. The surgeon then positions the lower sections 138 of each of the blades adjacent to the incision and pushes down on the retractor or otherwise manipulates the blades and the patient so the blades are pushed through the incision and past the sternum.

After inserting the retractor, the surgeon displaces the two retractor arm segments 112,116 with respect to each other by rotating the handle 118 on the second arm segment 116. As the surgeon opens the sternum of the patient, they also release any underlying connective tissue and open the pericardium surrounding the heart of the patient. In order to provide for visualization of the heart, the pericardium that surrounds the heart is retracted by placing sutures (not shown) through the pericardium and then threading the sutures through the slots 123 on the retractor arms to ensure that the sutures are spaced apart from the operative field. As mentioned above, the clamps (not shown) holding the sutures may then be positioned in the slots so that the distal end of the clamping instrument is positioned in the through holes 124. This allows the sutures and clamps to be positioned out of the way of the surgeon for the subsequent procedure. After performing any subsequent actions to further open the sternum of the patient to create the desired field of view and assess the viability of the heart to perform the bypass grafting procedure on one or more vessels, the surgeon mounts the stabilization arm system 104 onto one of the retractor arm segments 112,116 or the rack segment 114 in the position that they anticipate will provide the best access while minimizing the obstruction of their view for the particular procedure.

It should be recognized that the bypass grafting procedure may involve the arteries or branches thereof on nearly any surface of the heart including the posterior or backside of the heart. Therefore, having the capability to mount the stabilization arm system to the rack segment 114 or either of the arms, 112 or 116, of the retractor can be particularly advantageous. With the preferred form of the present invention, the stabilization arm system 104 may be positioned near the top of the operative field on the rack segment 114 rather than only along the sides of the operative field. The retractor 102 is typically arranged on the body so the throat of the retractor faces the head of the patient and the surgeon is typically located on one side of the patient while An assistant is located on the other side of the patient and instruments are passed across the body of the patient throughout the procedure. Therefore, with the preferred form of the present invention, the surgeon has an additional surface to choose from when they are deciding which surface will provide the best access to the desired surface of the heart while not interfering with the procedure.

To mount the stabilization arm system 104 onto the retractor 102, the surgeon rotates the sled actuator lever 154 of the sled member 141 so the second lip 152 is in a disengaged position and is spaced from the front edge lip 150 of the sled member 141. After so configuring the sled member 141 of the sled assembly 140, the surgeon positions the sled assembly 140 on the retractor 102 at any of a number of available positions on the arms, 112 and 116, or the rack segment 114 by positioning the front edge lip 150 over the front edge of the selected arm or rack segment. With the preferred configuration of the sled assembly 140, the surgeon need not slide the sled member along the entire length of a retractor arm or be required to select from a limited number of predetermined positions, but can place the sled member 141 of the sled assembly 140 directly at the desired position. In this way, a surgeon can removably position the sled assembly 140 anywhere on the rack segment 114 or the arms 112, 116 of the retractor 102 without having to first assemble the retractor with a sled assembly 140 initially positioned in any of these predefined areas. An advantage of this configuration is that the surgeon may initially position the sled member 141 of the sled assembly 140 in a position that they anticipate will be close to where they will ultimately want it.

If during the procedure, a different location is needed or provides better access, the surgeon may either slide the sled member 141 of the sled assembly 140 along the previously selected arm or rack segment to the desired location or they may remove the sled assembly 140 from the retractor and try various locations to see which location on the arms and rack segment provides the best access for the particular procedure. In addition, such a sled assembly configuration also allows the surgeon to perform certain surgical procedures without having to worry about the sled member 141 cutting or interfering with any sutures that may be passing over the retractor while positioning the sled assembly 140.

Furthermore, if multiple blood vessels are operated on or access to multiple surfaces is desired, the orientation of the sled assembly may be readily adjusted to accommodate the needs of the particular part of the procedure.

The surgeon may next fix the sled member in place by positioning the front edge lip 150 of the sled member 141 over the front edge surface 120a, 120b or 120c on the desired area of the retractor 102 and then rotating the sled actuator lever 154 partially or fully, as desired, so the second lip 152 contacts and engages the vertical extending surface of the corresponding step surface 122a–c on the retractor 102. Once the surgeon has placed the sled member of the sled assembly on the retractor, they may then initially position the stabilization device 106 near the ultimate desired location along the surface of the heart by loosening the movable knob 184 and rotating the fixed knob 186 as well as loosening the knob 160 on the mounting mechanism to orient the stabilization device 106 and stabilization arm system 104 in the tentative desired position. It should be recognized that this process may be repeated as often and whenever necessary to modify the position of the stabilization device 106 at the desired location or area of the heart or other tissue to be contacted.

Thereafter, the surgeon may loosen knob 160 and rotate the mounting mechanism 143 of the sled assembly 140 about the sled pin 158 and also move the handle segment 180 lengthwise and/or rotationally with respect to the sled assembly 140 to position the handle segment within the stabilization arm 162 clamp through aperture 164 so as to position the stabilization device 106 with respect to the predetermined area of the heart or other tissue to be contacted. Once the surgeon is satisfied with the location of the stabilization device 106 on the heart or other tissue of the patient, the surgeon may tighten knobs 160 and 184 to ensure that the stabilization arm system 104 and stabilization device 106 are retained in the desired position throughout the remainder of the procedure. Once the stabilization device 106 is in the desired contacting relationship with the predetermined area of the heart or other tissue, the surgeon may tighten the knob 160 of the sled assembly 140 so as to prevent further rotation about the threaded rod and the sled pin and also to prevent sliding of the handle segment in the aperture. The surgeon may also tighten the knob 184 of the handle segment 180 so as to tighten the connection between the distal connector 181 on the handle segment and the post member 196 on the stabilization device 106 prevent further motion of the stabilization device 106 about the end of the stabilization arm system 104.

After completing the grafting procedure, the surgeon may then remove the stabilization arm system 104 and stabilization device 106 by essentially reversing the above described steps or the surgeon may simply release the actuator lever 154 of the sled member 141 and remove the entire stabilization arm system and stabilization device from the operative field. Similarly, the actuator lever of the sled member may be moved to a position between the engaged and disengaged positions so that the stabilization arm system may be moved out of the way while a subsequent procedure is performed or to attach a new stabilization device thereon. Alternately, the knob may be rotated and the handle segment and stabilization device may be rotated out of the way or to the next desired location while the sled member is retained in the same position along the retractor.

In the foregoing discussion, the stabilization system of the present invention is described in terms of clamping and supporting a stabilization device. It is within the scope of the present invention, however, for the system to be configured to removably secure any of a number of surgical instrumentalities to the retractor or other operative base member. Additionally, although one stabilization arm is described as being in use at a time, it is within the scope of the present invention for plurality or a multiplicity of stabilization arms to be secured to the retractor. For example, one stabilization arm system could be provided to support a diaphragm retractor and another stabilization arm system provided to support a tissue stabilizer, suction device and/or a blower/mister device.

Although preferred embodiments of the invention have been described using specific terms, such description is for illustrative purposes only, and it is to be understood that changes and variations may be made without departing from the spirit or scope of the following claims.

What is claimed is:

1. A system for use in a surgical procedure on a patient, comprising:
    a retractor having a plurality of retractor arms thereon wherein said retractor arms are movable with respect to each other;
    a sled assembly operatively mountable to said retractor and said sled assembly including a mounting mechanism being sized to hold a medical device in a desired position during a medical procedure;
    the sled assembly including upper and lower portions wherein said upper portion is a mounting mechanism that is movable about the lower portion and the lower portion is a sled member that is connectable to the retractor; and
    the mounting mechanism being movable in a plurality of directions relative to the retractor and the medical device is movable horizontally and vertically relative to the retractor in response to three dimensional movement of the sled assembly by a single knob relative to the retractor.

2. The system of claim 1 wherein said retractor includes a plurality of retractor arms and an interconnecting segment and said sled member is slidable along at least a portion of each of said retractor arms and said interconnecting segment.

3. The system of claim 2 wherein each of said retractor arms and said interconnecting segment have a top surface and said sled member is slidable therealong on each of said retractor arms and said interconnecting segment.

4. The system of claim 1 wherein said mounting mechanism is compressible about the medical device in response to rotational movement of a member on the upper portion of the connector.

5. The system of claim 4 wherein movement of said member on mounting mechanism in a first direction engages the medical device and movement of the member in a second direction enables the movement of the medical device in the mounting mechanism.

6. The system of claim 1 wherein said sled member includes a first member on the lower portion thereof and the first member is movable between engaged and disengaged positions to engage and disengage said sled assembly from said retractor and at least a portion of said mounting mechanism is rotatable with respect to said retractor in said engaged and disengaged positions of said first member on the lower portion of the sled member.

7. The system of claim 6 wherein said first member thereon is movable between engaged and disengaged positions to engage and disengage the sled assembly from said retractor and said sled member is slidable with respect to said retractor in a partially disengaged position of said first member and fixedly engaged in non-slidable contact with respect to said retractor in said engaged position of said first member.

8. The system of claim 7 wherein said mounting mechanism is movable between engaged and disengaged positions to engage and disengage the medical device and said mounting mechanism is movable relative to said retractor in said engaged and disengaged positions of said first member.

9. The system of claim 1 wherein said sled member includes a pin member extending between the upper and lower portions of said sled member and said pin member is contacted by a pin clamp member that is movable between engaged and disengaged positions to engage and disengage said pin member to fixedly retain the mounting mechanism with respect to the sled member in the engaged position and to allow movement there between in the disengaged position.

10. The system of claim 1 wherein said mounting mechanism includes an elongate rod member extending lengthwise therealong and said rod member is movable to actuate a stabilization clamp member that is movable between engaged and disengaged positions to allow the rotational movement of the mounting mechanism relative to the retractor in the disengaged position and to prevent the rotational movement of the mounting mechanism relative to the retractor in the engaged position.

11. A system for use in a surgical procedure, comprising:
    a retractor having a plurality of generally planar retractor arms thereon and a segment interconnecting said retractor arms wherein said retractor arms are movable with respect to each other;
    a sled assembly operatively positionable with respect to said retractor and including a mounting mechanism that is sized to hold a medical device in a desired position during a medical procedure;
    a sled member which is attachable in a fixed position on said retractor and which interacts with said mounting mechanism of said sled assembly to hold said medical device in the desired position during the medical procedure; and
    said sled assembly including upper and lower portions wherein said lower portion selectively engages said retractor and said upper portion includes said mounting mechanism to selectively engage said medical device and wherein said mounting mechanism includes a plurality of clamp members thereon to engage and disengage relative movement between the upper and lower portion of said sled assembly and to engage and disengage movement of said medical device relative to said retractor.

12. The system of claim 11 wherein movement between the upper and lower portions of said sled assembly is in a direction generally parallel to the planar surface of the retractor.

13. The system of claim 11 wherein said plurality of clamps on said mounting mechanism includes a pin clamp member thereon that operates between engaged and disengaged positions to engage and disengage said upper portion of said sled assembly from said lower portion of said sled assembly such that said upper portion is movable with respect to said lower portion in the disengaged position of said pin clamp member and movement of said upper portion with respect to said lower portion of said sled assembly is restricted in the engaged position of the pin clamp member.

14. The system of claim 13 wherein said sled assembly includes a pin member extending between said upper portion and said lower portion and said pin clamp member engages said pin member in said engaged position of said pin clamp member.

15. The system of claim 13 wherein said sled assembly is movable along said retractor in said engaged and disengaged positions of said pin clamp member.

16. The system of claim 11 wherein movement between the mounting member of the upper portion of said sled assembly and the sled member of the lower portion of the sled assembly is generally parallel to the planar surface of the retractor.

17. The system of claim 16 wherein a plurality of clamps on said sled assembly includes a stabilization clamp member thereon that operates between engaged and disengaged positions to engage and disengage said medical device with respect to said upper portion of said sled assembly such that said medical device is movable in a generally three dimensional direction with respect to said retractor in the disengaged position of said stabilization clamp member and movement of said medical device with respect to said upper portion of said sled assembly is restricted in the engaged position of the stabilization clamp member.

18. The system of claim 17 wherein said sled assembly is movable along said retractor in said engaged and disengaged positions of said stabilization clamp member.

19. The system of claim 11 wherein said retractor includes a plurality of arms and an interconnecting segment thereon and said sled assembly is slidable along said interconnecting segment of said retractor in said engaged and disengaged positions of said plurality of clamp members of said mounting mechanism.

20. The system of claim 19 wherein said lower portion includes a lever member thereon and said lever member is moveable between engaged and disengaged positions thereon to fixedly connect said sled assembly to said retractor in said engaged position.

21. The system of claim 20 wherein said lever member is movable to an intermediate position wherein said lower portion slidingly engages at least a portion of said retractor and said sled assembly is slidable therealong.

22. The system of claim 11 wherein said upper portion of said sled assembly includes an elongate member thereon that is oriented generally parallel to the planar surface of the retractor and said elongate member interconnects at least two of the plurality of clamp members thereon.

23. The system of claim 22 wherein the plurality of clamp members include a pin clamp member and a stabilization clamp member on the upper portion of the sled assembly and wherein the elongate member is movable to an engaged position wherein rotational movement of the upper portion of the sled assembly relative to the retractor is limited.

24. The system of claim 23 wherein rotational movement of the upper portion of the sled assembly relative to the lower portion of the sled assembly is prevented in the engaged position of the pin clamp member.

25. The system of claim 23 wherein said plurality of clamp members include a stabilization clamp member that engages said medical device and said stabilization clamp member is offset from an axis of rotation of said elongate member formed between said upper potion and said lower portion of said sled assembly.

26. The system of claim 23 wherein said pin clamp member is movable between engaged and disengaged positions and wherein rotational movement between said upper portion and said lower portion of said sled assembly is oriented generally parallel to the planar surface of the retractor and the stabilization clamp member is movable between engaged and disengaged positions and wherein rotational movement of said stabilization clamp member is generally perpendicular to the planar surface of the retractor.

27. The system of claim 22 wherein said elongate member includes an axis of rotation on said sled assembly and at least one of the plurality of clamp members is offset therefrom on said upper portion of said sled assembly.

28. The system of claim 27 wherein said plurality of clamp members include a pin clamp member and said pin clamp member is aligned with said axis of rotation of said elongate member between said upper portion and said lower portion of said sled assembly.

29. A system for use in a surgical procedure, comprising:
   a retractor having a plurality of laterally extending arms thereon wherein said arms are movable with respect to each other and said retractor includes a top and generally planar surface;
   a sled assembly operatively positionable with respect to said retractor and including an upper portion with a mounting mechanism thereon to hold a medical device in a desired position during a medical procedure;
   the upper portion of the sled assembly is movable with respect to the lower portion of the sled assembly and the mounting mechanism is movable with respect to the retractor and includes opposite end portions thereon;
   the mounting mechanism including an elongate member having a rotational axis and extending generally between the opposite ends of the mounting mechanism; and
   said medical device is releasably retained on the upper portion of the sled assembly.

30. The system of claim 29 wherein said mounting mechanism is generally offset from the rotational axis of the elongate member formed between the upper portion and the lower portion of the sled assembly.

31. The system of claim 29 wherein said upper portion and said lower portion of said sled assembly include a pin member extending therebetween and a first clamp member on said upper portion and said first clamp member is movable between engaged and disengaged positions wherein rotational movement between said upper and lower portions is prevented in the engaged position of said first clamp member.

32. The system of claim 31 wherein rotation of said first clamp member is generally perpendicular to the rotational axis of the elongate member.

33. The system of claim 31 wherein rotation of said first clamp member is generally parallel to the planar surface of the retractor.

34. The system of claim 31 wherein said first clamp member permits rotational movement between the upper portion and the lower portion of the sled assembly in a generally horizontal direction.

35. The system of claim 29 wherein said opposite ends of said upper portion are oriented in a generally horizontal direction along said sled assembly and are spaced apart from said top surface of said retractor.

36. The system of claim 29 wherein said upper portion of said sled assembly includes a second clamp member extending therealong and said second clamp member is movable between engaged and disengaged positions wherein rotational movement between said medical device and said elongate member is permitted in the disengaged position of said second clamp member.

37. The system of claim 36 wherein said second clamp member is offset from the rotational axis of the elongate member and rotational movement of the second clamp member is generally perpendicular to the planar surface of the retractor.

38. The system of claim 36 wherein said second clamp member is generally spaced apart from one of said opposite ends of said upper portion and is generally adjacent to said first clamp member along the elongate member.

39. The system of claim 36 wherein said second clamp member permits rotation of at least a portion of said upper portion and the medical device in a generally vertical direction in the disengaged position.

40. The system of claim 39 wherein said second clamp member permits rotation of said medical device in a direction that is generally perpendicular to the planar surface of the retractor in the disengaged position thereof.

41. The system of claim 29 wherein said sled assembly includes first and second clamp members and said medical device is movable in generally parallel and perpendicular directions relative to said planar surface of said retractor when said first and second clamp members are in the disengaged positions.

42. The system of claim 41 wherein said sled assembly is movable relative to said retractor when said first and second clamp members are in the engaged and disengaged positions.

43. The system of claim 41 wherein at least one of said first and second clamp members are spaced apart from one said of said opposite ends of said upper portion of said sled assembly.

44. The system of claim 41 wherein each of said first and second clamp members are spaced apart from one of said opposite ends of said upper portion of said sled assembly.

45. The system of claim 41 wherein said at least one of said first and second clamp members are offset from a rotational axis formed between said upper portion and said lower portion of said sled assembly.

46. The system of claim 45 wherein each of said first and second clamp members are offset from the rotational axis of elongate member of said mounting mechanism.

47. The system of claim 29 wherein said lower portion of said sled assembly includes an actuation lever movable between engaged and disengaged positions and said sled assembly is movable along said retractor in the disengaged position thereof and is fixedly connected thereto in the engaged position of the actuation lever and wherein the upper portion is movable relative to the lower portion irk the engaged and disengaged positions of the actuation lever.

48. The system of claim 47 wherein the actuation lever is rotatable less than about 180 degrees between the engaged and disengaged positions about an offset pin member.

49. A system for supporting a surgical instrument, comprising:
   a retractor;
   a surgical instrument support that secures the surgical instrument to the retractor;
   wherein the surgical instrument support includes:
      (a) a sled assembly having an upper portion and a lower portion;
      (b) the lower portion releasably engaging the retractor at a desired location therealong and the upper portion releasably engaging a surgical instrument and wherein the upper portion is rotatable with respect to the lower portion in a generally horizontal direction and the surgical instrument is movable with respect to the retractor in a generally three dimensional direction;
      (c) a mounting mechanism including a pair of clamp members thereon which are each movable between engaged and disengaged positions wherein when one of the clamp members is in the engaged position, rotation of the upper portion with respect to the lower portion is prevented and when the other of the clamp members is in the engaged position movement of the surgical instrument with respect to the upper portion is prevented.

50. The system of claim 49 wherein the mounting mechanism is an elongate member that has an axis of rotation in the lengthwise dimension which extends between a knob member and a surgical instrument engaging clamp.

51. The system of claim 49 wherein the mounting mechanism thereon and wherein the mounting mechanism includes a knob member and the knob member is in operative contact with a lower portion engaging clamp, a surgical instrument rotating clamp and a surgical instrument engaging clamp.

52. The system of claim 51 wherein each of the lower portion engaging clamp, surgical instrument rotating clamp and the surgical instrument engaging clamp are rotatable with respect to each and are engaged and disengaged upon actuation of the knob member.

53. A system for stabilizing a predetermined area of a patient, comprising:
   a retractor;
   a stabilization device sized to be positioned adjacent to the desired predetermined area of a patient;
   an elongate stabilizer arm that engages the stabilization device;
   a sled assembly for interconnecting the stabilizer are to the retractor;
   wherein the retractor includes:
      two arms and a rack segment, interconnecting the two arms, for selectively spacing the two arms from each other and for maintaining the two arms in a desired fixed relationship, and
      wherein at least one of the two arms and rack segment are configured to removably receive the sled assembly connected thereto; and
   wherein the sled assembly includes:
      a sled member on the sled assembly for connecting the handle to the retractor so the stabilization device can be moved to a desired position wherein the stabilization device engages the predetermined area of the patient and the sled assembly further including a mounting mechanism forming an upper portion thereof and the sled member forming a lower portion wherein the upper portion includes a plurality of clamp members rotatable about a horizontal axis of the upper portion thereon and the plurality of clamp members enable the stabilization arm to move in vertical and horizontal directions relative to the retractor in a disengaged position and prevent the relative movement thereof in the engaged position and the lower portion including a clamp member having an engaged position wherein movement of the connector relative to the retractor is prevented and a disengaged position wherein movement of the connector relative to the retractor is permitted and wherein the stabilization arm is movable relative to the retractor in the engaged and disengaged position of the clamp member on the lower portion.

54. A system for supporting a surgical instrument, comprising:
   a retractor having a plurality of arms having front edges facing each other thereon;

a sled assembly that secures a surgical instrument to the retractor;

wherein the sled assembly includes:
(a) a lower portion and an upper portion; and
(b) the lower portion including a clamp thereon to releasably engage the retractor at a desired location therealong and the upper portion including a plurality of clamp members thereon and wherein the clamp members releasably engage the surgical instrument and wherein the upper portion is rotatable with respect to the lower portion about a first axis and the surgical instrument is movable with respect to at least a portion of the upper portion about a second axis and said first axis and said second axis are generally perpendicular to each other.

55. The system of claim 54 further including knob member on said upper portion which is rotatable to move at least one of the clamp members thereon between engaged and disengaged positions wherein when the knob member is in the engaged position, rotation of the upper portion with respect to the lower portion is prevented and movement of the surgical instrument with respect to at least a portion of the upper portion is prevented.

56. A system for supporting a surgical instrument, comprising:

a surgical platform sized for positioning adjacent to the body of a patient, and the platform having at least one elongate member thereon having at least one front edge extending there along and facing an incision in the body of the patient;

a sled assembly that secures a surgical instrument to the surgical platform;

wherein sled assembly includes:
(a) lower portion and an upper portion; and
(b) the lower portion including a clamp member thereon for releasably engaging the surgical platform at a desired location therealong and the upper portion including a plurality of clamp members thereon releasably engaging the surgical instrument and wherein the upper portion is rotatable with respect to the lower portion about a first axis and the surgical instrument is movable with respect to at least a portion of the upper portion about a second axis and said first axis and said second axis are generally perpendicular to each other and said first axis is generally parallel to said surgical platform.

57. The system of claim 56 further including knob member on said upper portion which is rotatable between engaged and disengaged positions wherein when the knob member is in the engaged position, rotation of the upper portion with respect to the lower portion is prevented and movement of the surgical instrument with respect to at least a portion of the upper portion is prevented while the movement of the sled assembly along the surgical platform is allowed.

* * * * *